United States Patent
Baert et al.

(10) Patent No.: US 6,365,188 B1
(45) Date of Patent: Apr. 2, 2002

(54) SOLID MIXTURES OF CYCLODEXTRINS PREPARED VIA MELTEXTRUSION

(75) Inventors: Lieven Elvire Colette Baert, Brugge; Jozef Peeters, Beerse; Geert Verreck, Malle, all of (BE)

(73) Assignee: Janssen Pharmaceutica, N.V., Beerse (BE)

( * ) Notice: Subject to any disclaimer, the term of this patent is extended or adjusted under 35 U.S.C. 154(b) by 0 days.

(21) Appl. No.: 09/081,808

(22) Filed: May 20, 1998

(51) Int. Cl.$^7$ .............................. A61K 9/14; A61K 9/20
(52) U.S. Cl. ...................... 424/488; 424/489; 424/464
(58) Field of Search ................... 424/488, 489, 424/464

(56) References Cited

U.S. PATENT DOCUMENTS

| | | | |
|---|---|---|---|
| 4,722,815 A | * | 2/1988 | Shibanal .................... 264/117 |
| 5,009,900 A | | 4/1991 | Levine et al. |
| 6,039,981 A | | 3/2000 | Woo et al. |

FOREIGN PATENT DOCUMENTS

| | | | |
|---|---|---|---|
| EP | 0 665 009 A1 | | 8/1995 |
| FR | 2 705 677 | | 12/1994 |
| JP | WO 94/11031 | | 5/1994 |
| WO | WO 97/18839 | * | 5/1997 |

OTHER PUBLICATIONS

Fumitoshi Hirayama, Zheng Wang, and Kaneto Uekama, "Effect of 2–Hydroxypropyl–β–cyclodextrin on Crystallization and Polymorphic Transition of Nifedipine in Solid State", Nov. 12, 1994, Pharmaceutical Research, 1766–1770.

John S. Hostetler, Linda H. Hanson, and David A. Stevens, "Effect of 2–Hydroxypropyl–β–cyclodextrin on efficacy of oral itraconazole I disseminated murine cryptococcosis", Apr. 24, 1993, Journal of Antimicrobial Chemotherapy, 459–464.

Yuzuru Mikami, Tomoko Sakamoto, Katsukiyo Yazawa, Yasushi Tanaka, and Akihiro Matsumae,"Effects of Solvents on the Manifestation of the Activity of the New Antimycotic Agent Intraconazole in a Mouse Infection Model", Feb. 8, 1994, Jpn. J. Med. Mycol., 263–267.

H. Van Doorne, E.H. Bosch, and C.F. Lerk, "Formation and antimicrobial activity of complexes of β–cyclodextrin and some antimycotic imidazole derivatives", Pharmaceutisch Weekblad Scientific Edition, vol. 10.

Kaneto Uekama, Kengo Ikegami, Zheng Wang, Yasuhide Horiuchi, and Fumitoshi Hirayama, "Inhibitory Effect of 2–Hydroxypropyl–β–cyclodextrin on Crystal–growth of Nifedipine During Storage: Superior Dissolution and Oral Bioavailability Compared with Polyvinylpyrrolidone K–30", Feb. 19, 1991, J. Pharm. Pharmacol., 73–78.

* cited by examiner

Primary Examiner—Thurman K. Page
Assistant Examiner—Todd D Ware
(74) Attorney, Agent, or Firm—Mary A. Appollina (57) ABSTRACT

Process for preparing a solid mixture comprising one or more cyclodextrins and an insoluble active ingredient characterized in that said process comprises a melt-extrusion step, wherein the active ingredient is embedded into the cyclodextrin carrier.

9 Claims, 7 Drawing Sheets

SOLID MIXTURES OF CYCLODEXTRINS PREPARED VIA MELTEXTRUSION

CROSS REFERENCE TO RELATED APPLICATIONS

This application is a National Stage application under 35 U.S.C. 371 of PCT/EP96/05118 filed Nov. 20, 1996, which claims priority from EP95.203.219.1, filed Nov. 23, 1995.

The present invention involves a process for preparing solid mixtures by melt-extrusion comprising one or more active ingredients, preferably one or more practically insoluble active ingredients and one or more cyclodextrins. The invention further concerns pharmaceutical compositions comprising the above mixture.

WO 94/11031, published on May 5, 1994, discloses a method of manufacturing a high-quality enclosure compound using extrusion techniques. In this document the extrusion of cyclodextrins together with an active ingredient is mentioned. However, the document discloses the use of a wet mixture (i.e. including water or another solvent) to feed into the extruder. French patent application 2,705,677 published on Dec. 2, 1994 describes micro-granules obtained by extrusion-spheronisation containing a cyclodextrin. The extrusion-spheronisation technique is the combination of an agglomeration technique, i.e. extrusion, and a shaping technique, i.e. the spheronisation. Said patent application actually teaches the formation of microgranulates containing β-cyclodextrin (Kleptose®) and microcrystalline cellulose (Avicel®) and as active ingredients ketoprofen and paracetamol. The extrusion technique used in the above-mentioned patent application consists in preforming a humid mass by forcing said human mass through a nozzle thus forming long strands of extruded material. The document does not mention melt-extrusion at all.

EP 0,665,009, published as international application on Apr. 24, 1994, discloses a method of dislocating the crystalline condition of crystalline medicine by extruding said crystalline material as such, i.e. without any excipient such as cyclodextrins. In J. Pharm. Pharmacolog., vol 44, No 2, pages 73–8, Uekama et al show how amorphous nifedipine powders were prepared by spray-drying with hydroxypropyl-β-cyclodextrins. The document does not mention melt-extrusion.

In Pharm. Weekbl. Sci. Ed., 1988, vol 10, No 2, page(s) 80–85, Van Doorne et al, the complex formation between β-cyclodextrins and six antimicotic imidazole derivatives was studied. In said study gels and creams comprising antimicotics were prepared whereby a 1.8% solution of β-cyclodextrin was added instead of purified water. There is no mentioning of extrusion at all. In J. Antimicrob. Chemother., 1993, vol 32, No 3, pages 459–463, Hostetler et al describe the effect of hydroxypropyl-β-cyclodextrin on the efficacy of oral itraconazole in disseminated murine cryptococcosis. In said document the authors describe how itraconazole is solubilized in hydroxypropyl-β-cyclodextrin resulting in a 100 ml solution. There is no mentioning at all of an extrusion process. In Jpn. J. Med. Mycol., 1994, vol 35, No 3, page 263–267, Mikami et al describe the effect of carrier solvents on the efficacy of oral itraconazole therapy in aspergilosssis in mice. Again this document discloses itraconazole being solubilized in hydroxypropyl-β-cyclodextrin. There is no mentioning of extrusion techniques.

In "Effect of 2-Hydroxypropyl-β-cyclodextrin on Crystallization and Polymorphic Transition of Nifedipine in Solid State", Pharmaceutical research, vol 11, No 12, 1994, Uekama et al. describe a glassy mixture of 2-hydroxypropyl-β-cyclodextrin obtained by heating said mixture and immediately cooling said mixture to 0 degrees Celsius. There is no teaching that this mixture can be extruded.

U.S. Pat. No. 5,009,900 describe glassy matrices that are useful for introducing and/or retaining and/or stabilizing the volatile and/or labile components in cooked and uncooked food products. These glassy matrices comprise chemically modified starch having a dextrose equivalent not greater than about 2; maltodextrin, corn syrup solids or a polydextrose, and a mono- or disaccharide. The document does disclose extrusion to form glassy matrices. However, there is no specific mentioning of cyclodextrins and of therapeutically or pharmaceutically active ingredients.

None of the above mentioned documents disclose the present invention.

Although WO 94/11031 and French patent application 2,705,677 disclose extrusion of mixtures of cyclodextrins and actives ingredients, said documents do not mention the use of meltextrusion. The technique described in WO 94/11031 and French patent application 2,705,677 has a main disadvantage, that a humid mass needs to be prepared which requires adding to the cyclodextrin and the active ingredient a certain amount of water and in most cases others solvents such as ethanol or methanol. Removing the water and/or other solvents is often a troublesome production step, which often leads to irreproducibiity because not all of the solvent can be removed. Moreover, with practically insoluble active ingredients the amounts of water and/or adjuvant solvents needed make the above technique unpractical on a production scale. Another disadvantage of the technique described in the prior art is that the drying step can induce unwanted crystallization of the active ingredient.

These problems are solved in the present invention by the use of a melt-extrusion process to form solid mixtures comprising one or more cyclodextrins and insoluble active ingredients.

The present process is advantageously applicable when said active ingredient is sensitive to a solvent such as water or an organic solvent, because it does not require any solvent. The term "sensitive" used herein means that the active ingredient is readily (e.g. within about one hour) influenced by a solvent to such an extent that its physical, chemical and/or biological properties are substantially modified or changed.

The present process is further advantageous because it does not require a drying step, during which insoluble active ingredients often tend to crystallize.

The term "insoluble" hereinabove and hereinunder refers to three categories of compounds, i.e. the "very slightly soluble", "practically insoluble" and "insoluble".

The terms "very slightly soluble", "practically insoluble" or "insoluble" are to be understood as defined in the United States Pharmacopeia 23, NF 18 (1995) page 7, i.e. a "very slightly soluble" compound requires from 1000 to 10,000 parts of solvent for 1 part of solute; a "practically insoluble" or "insoluble" compound requires more than 10,000 parts of solvent for 1 part of solute. The solute referred to in these cases are water or aqueous solutions.

Three examples of this type of insoluble compounds are: itraconazole, loviride and (±)-ethyl (R*,R*)-4-[5-[1-[1-[(4-chlorophenyl)hydroxymethyl]propyl]-1,5-dihydro-5-oxo-4H-1,2,4-triazol-4-yl]-2-pyridinyl]-1-piperazinecarboxylate (hereinafter referred to as compound 1).

Itraconazole is an art-known antifungal. Loviride is an art-known anti-retrovirally active compound, particularly useful in treating HIV-infected patients. (±)-Ethyl (R*,R*)-4-[5-[1-[1-[(4-chlorophenyl) hydroxymethyopyl]propyl]-1,5-dihydro-5-oxo-4H-1,2,4-triazol4-yl]-2-pyridinyl]-1-piperazinecarboxylate is described as compound No. 3, in WO 95/27704 published on Oct. 19, 1995.

The compounds that are suitable to be used in this technique are compounds that show no appreciable decomposition at the temperatures needed to melt and extrude the mixture of said one or more active ingredients with the cyclodextrin or cyclodextrins.

The term "active ingredient" further refers to compounds or mixtures of compounds which are pharmaceutically or therapeutically or cosmetically active for treating humans or animals.

The present invention provides a process for preparing a solid mixture comprising one or more cyclodextrins and an (insoluble) active ingredient, comprising a melt-extrusion step wherein one or more cyclodextrins are combined with the one or more active ingredients.

Melt-extrusion is a polymer extrusion technique which involves embedding an active ingredient in one or more carriers. In this technique the active ingredient and excipients are molten in the extruder and hence embedded in thermoplastic and thermomelting polymers. The resulting molten mass is then forced through one or more nozzles resulting in a thermoplastic strand or strands.

Figure 1:
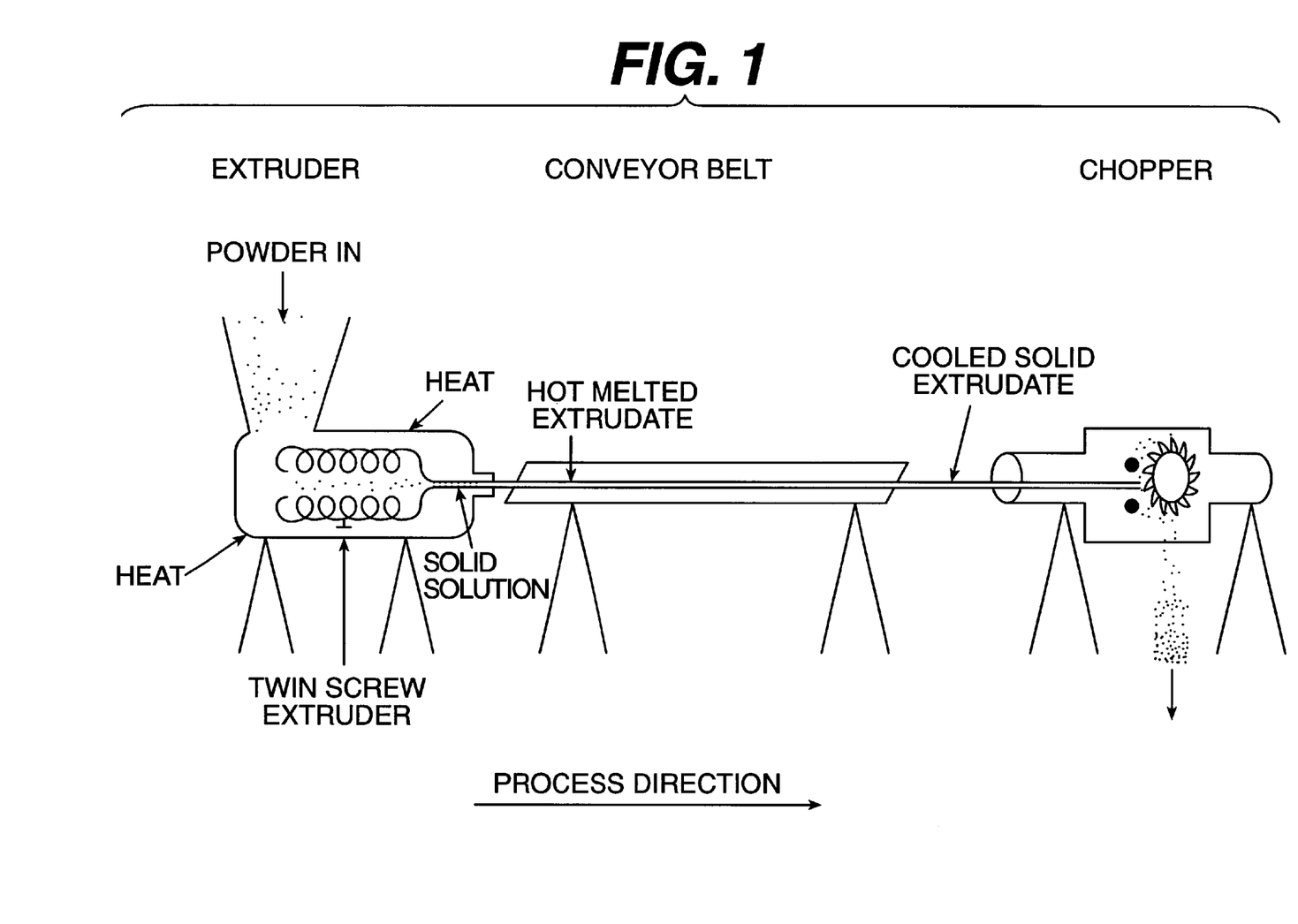
FIG. 1 is a schematic representation of a configuration for carrying out the present invention.

An extruder comprises an inlet structure, a cylindrical structure called "barrel", a die and a screw or screws. A schematic overview is shown in FIG. 1.

The inlet structure mostly is funnel shaped.

The barrel may comprise one or more barrel units and the screw or screws extend through them.

Extruders are available in two general types, namely a single-screw extruder comprising one screw and a multi-screw extruder comprising two or more screws. While this invention can be carried out using either type of extruder, the use of a multi-screw extruder, particularly a twin-screw extruder is preferred. A twin-screw extruder (and a multi-screw extruder) is more efficient in that the plural screws interfering with each other precludes follow-up movement of the active ingredient and, moreover, the intermeshing of the screws provides a high energy output physically.

An interesting mode of operating the screws is to operate them in a corotating mode.

The screw or screws may have different shapes such as, for example, a trapezoidal screw, a trapezoidal cut screw, trapezoidal reverse cut screw, ball screw, kneading paddle and these may be used in the desired combination.

The load fed into the extruder via the inlet structure is forced by the screw or screws to advance, shorn and blended by the screw within the barrel and extruded from the orifice or orifices of the die. The temperature of the barrel or of the barrel units can be controlled via a heating element or even if necessary by a cooling element.

The rotational speed of the screw can be set within the allowable range of the extruder used.

A person skilled in the art is able to select the screw geometry and combination of unit screws. The principal function of the screw is to transport, crush and knead the material that is being extruded.

The orifice configuration may be circular, elliptical, rectangular or hexagonal.

Hence, said melt-extrusion step comprises the following substeps:
 a) mixing one or more cyclodextrins with the active ingredient or active ingredients,
 b) optionally mixing additives,
 c) heating the thus obtained mixture until melting of one of the components,
 d) forcing the thus obtained mixture through one or more nozzles;
 e) cooling the mixture till it solidifies.

If desired, as mentioned above, the thermomelting mixture comprising one or more cyclodextrins and active ingredient(s) may comprise any suitable additive. When, for instance, the cyclodextrin(s) or the active ingredient(s) or one of the other possible additives is apt to be oxidized, an anti-oxidizing agent may be incorporated, preferably in small amounts, such as, for instance 100 to 5000 ppm when compared to the total weight of the mixture. Furthermore, conventional auxiliary additives such as pigments, flavors, stabilizers, preservatives and buffers may be added.

If necessary conventional pharmacologically acceptable plasticizers, such as long chain alcohols, ethylene glycol, propylene glycol, thriethylene glycol, butanediols, pentanols, hexanols, polyethylene glycols, aromatic carboxylates (e.g. dialkyl phthalates, trimellitates, benzoates or terephthalates), aliphatic dicarboxylates or fatty acid esters can also be added. Preferably however, a plasticizer is not needed.

The term "melting" should be broadly interpreted. "Melting" can also refer to the fact that some transition is made to a glassy state, in which it is possible for one component of the mixture to get embedded into the other. In particular cases, one component will melt and the other component(s) will dissolve in the melt thus forming solid solutions, which show advantageous dissolution properties.

The possible formation of these solid solutions is one of the further advantages of the present invention. It will be appreciated by a person skilled in the art that mixing two or more solids, i.e. one or more cyclodextrins and the active ingredient or ingredients, and subsequently melting these solids together will give rise to different products than when the said solids are first brought into contact with water or another solvent and then extruded.

A characteristic of the melt extruded mixtures of the present invention is the fact that they contain substantially less water or any other solvent than mixtures being extruded in an other way.

Preferably the present melt extruded mixtures contain no water or solvent, apart from the water or solvent that eventually is contained in the crystal structure of the active ingredient.

It will be appreciated that the temperature inside the extruder is an important parameter. When different barrel units are present, different temperatures can be applied. A person skilled in the art is able to establish the required temperatures by taking the desired type of cyclodextrin or cyclodextrins or even the complete mixture that is going to be extruded and observing the behavior as a function of temperature with the aid of a melting point measuring instrument, such as a Kofler hot bench, a microscope hot stage type or a differential scanning calorimeter, e.g. type DSC 7 Series - Perkin Elmer.

The cooling can be performed without using any auxiliary means, i.e. it most often suffices to let the thermoplastic strand coming out of the extruder cool down to the ambient temperature of the production site. Of course, cooling aids may be used.

Once these thermoplastic strands are cooled down these strands can be milled to obtain a powdered form of the mixture of cyclodextrin or cyclodextrins and the active ingredient.

A person skilled in the art will appreciate that the milling can influence the physical characteristics of the extrudate. During milling the temperature of the material can rise because of the friction and also high shear forces are exerted on the material that is to be milled. Both temperature and mechanical or shear forces can result in a transition of the physical state of the material that is to be milled. A person skilled in the art has sufficient means at his disposal to control temperature and shear forces and thus to control the milling process.

The two processes, i.e. melt extrusion and milling can be combined into one configuration as is shown in FIG. 1. The mixture of one or more cyclodextrins and one or more active ingredients in combination with possible other additives is feed via a funnel like inlet. The mixture is then melt-extruded and the mixture is forced through a nozzle onto a conveyor belt. While being transported on the conveyor belt the extrudate cools down. The cooled melt extrudate is fed into a chopper which forms pellets. These pellets may be further milled if required.

This powdered material still has the beneficial properties (high bioavailability, dissolution rate, etc.) and it can be used in the conventional way to prepare pharmaceutical, therapeutical or cosmetical solid dosage forms.

An additional advantage of the present invention is that the active ingredient as well as the cyclodextrins may be transformed in a amorphous form or even that a solid solution is formed. A person skilled in the art will appreciate that this modification of physical state from crystalline to amorphous or to solid solutions is highly advantageous for the dissolution.

The fact whether the melt extruded mixture contains amorphous material or contains a solid solution or consists essentially of amorphous material or a solid solution can be measured or checked using differential scanning calorimetry. When there is crystalline material present in the melt extruded mixture a differential scanning calorimeter will show an endothermic melting peak. When amorphous material or a solid solution is mainly present in the melt extruded mixture a differential scanning calorimeter will not show an endothermic melting peak. Visual inspection of the melt extrudate allows for a distinction between amorphous material and a solid solution. In case the melt extrudate is opaque then both the cyclodextrin(s) and the active ingredient are in a amorphous form. In case melt extrudate is clear then a solid solution was formed.

Curves of differential scanning calorimetry are shown in FIGS. 2 to 7.

Interesting embodiments of the present invention are these melt extruded mixtures which consist mainly of amorphous material.

More interesting embodiments of the present invention are these melt extruded mixtures which consist essentially of amorphous material.

Even more interesting embodiments of the present invention are those melt extruded mixtures which consist mainly of a solid solution of the active ingredient or active ingredients in the cyclodextrin or the cyclodextrins.

Preferred embodiments of the present invention are those melt extruded mixtures which consist essentially of a solid solution of the active ingredient or active ingredients in the cyclodextrin or the cyclodextrins.

Another advantage of the present invention is that the granulation step in forming pharmaceutical, therapeutical or cosmetical compositions can be omitted, because the powdered material can simply be mixed with other excipients and compressed into, for instance, tablets or another solid pharmaceutical, therapeutical or cosmetical form.

Depending upon the characteristics of the melt extruded mixture, the size of the pellets of said melt extruded mixture or the mesh of the powder of said melt extruded mixture and, of course, dependent upon the other auxiliaries that are added to the unit dosage forms the unit dosage form may give immediate release or sustained release.

If desired, said solid pharmaceutical form may also be provided with a conventional coating to improve the appearance and/or the flavor (coated tablets) or additionally to target the release of the active ingredient.

Suitable tablets may have the following compositions and may be prepared in a conventional way. The amounts given are of course dependent upon the dose required for the pharmaceutical, therapeutic or cosmetic activity.

| Composition A | |
|---|---|
| milled melt extrudate | 100–500 mg |
| microcrystalline cellulose | 100–300 mg |
| crospovidone | 10–200 mg |
| colloidal silicon dioxide | 1–5 mg |
| sterotex | 2–10 mg |

| Composition B | |
|---|---|
| milled melt extrudate | 100–500 mg |
| Microcelac (TM) (1) | 200–300 mg |
| crospovidone | 70–200 mg |
| talc | 20–50 mg |
| sterotex | 7–10 mg |
| colloidal silicon dioxide | 1–5 mg |
| magnesium stearate | 2–10 mg |

The cyclodextrin to be used in the aforementioned compositions include the pharmaceutically acceptable unsubstituted and substituted cyclodextrins known in the art, more particularly α,β or γ cyclodextrins or the pharmaceutically acceptable derivatives thereof.

Substituted cyclodextrins which can be used in the invention include polyethers described in U.S. Pat. No. 3,459,731. In general, unsubstituted cyclodextrins are reacted with an alkylene oxide, preferably under superatmospheric pressure and at an elevated temperature, in the presence of an alkaline catalyst.

Since a hydroxy moiety of the cyclodextrin can be substituted by an alkylene oxide which itself can react with yet another molecule of alkylene oxide, the average molar substitution (MS) is used as a measure of the average number of moles of the substituting agent per glucose unit. The MS can be greater than 3 and theoretically has no limit.

Further substituted cyclodextrins are ethers wherein the hydrogen of one or more cyclodextrin hydroxy groups is replaced by $C_{1-6}$alkyl, hydroxy$C_{1-6}$alkyl, carboxy-$C_{1-6}$alkyl or $C_{1-6}$alkyloxycarbonyl$C_{1-6}$alkyl or mixed ethers thereof. In particular such substituted cyclodextrins are ethers wherein the hydrogen of one or more cyclodextrin hydroxy groups is replaced by $C_{1-3}$alkyl, hydroxy$C_{2-4}$alkyl or carboxy$C_{1-2}$alkyl or more in particular by methyl, ethyl, hydroxyethyl, hydroxypropyl, hydroxybutyl, carboxymethyl or carboxyethyl.

In the foregoing definitions the term "$C_{1-6}$alkyl" is meant to include straight and branched saturated hydrocarbon radicals, having from 1 to 6 carbon atoms, such as, methyl, ethyl, 1-methylethyl, 1,1-dimethylethyl, propyl, 2-methylpropyl, butyl, pentyl, hexyl and the like.

Such ethers can be prepared by reacting the starting cyclodextrin with an appropriate O-alkylating agent or a mixture of such agents in a concentration being selected so that the desired cyclodextrin ether is obtained. The said reaction is preferably conducted in a suitable solvent in the presence of an appropriate base. With such ethers, the degree of substitution (DS) is the average number of substituted hydroxy functions per glucose unit, the DS being thus 3 or less.

In the cyclodextrin derivatives for use in the compositions according to the present invention, the DS preferably is in the range of 0.125 to 3, in particular 0.3 to 2, more in particular 0.3 to 1 and the MS is in the range of 0.125 to 10, in particular of 0.3 to 3 and more in particular 0.3 to 1.5.

Of particular utility in the invention are the β-cyclodextrin ethers, e.g. dimethyl-β-cyclodextrin as described in Drugs of the Future, Vol. 9, No. 8, p. 577–578 by M. Nogradi (1984) and polyethers, e.g. hydroxypropyl β-cyclodextrin and hydroxyethyl β-cyclodextrin, being examples. Such an alkyl ether may be a methyl ether with a degree of substitution of about 0.125 to 3, e.g. about 0.3 to 2. Such a hydroxypropyl cyclodextrin may for example be formed from the reaction between β-cyclodextrin an propylene oxide and may have a MS value of about 0.125 to 10, e.g. about 0.3 to 3.

A more novel type of substituted cyclodextrins is sulfobutylcyclodextrines. These type are also envisaged in the present invention.

The ratio of active ingredient over cyclodextrin may vary widely. For example ratios of 1/100 to 100/1 may be applied. Interesting ratios of active ingredient over cyclodextrin range from about 1/10 to 10/1. More interesting ratios of active ingredient over cyclodextrin range from about 1/5 to 5/1. Most interesting ratios range from about 1/3 to 3/1. Preferred ratio is about 1/1.

The use of a mixture of cyclodextrins, either different types (α, β, γ) or different substitution (2-hydropropyl or methyl) or different substitution grades in sometimes recommendable to decrease the melting point.

EXAMPLE 1

Extruded samples of active ingredient with hydroxypropyl-β-cyclodextrin (HP-β-CD) were obtained using a Twin Screw Extruder type MP19 APV Baker (commercially available from the company APV Baker) with a die having a orifice of 3 mm. The process parameters for each individual experiment are shown in the table 1. This type of extruder has a L/D ratio of 15 and a screw pattern : 4D FS-4×30 FP-4×60 FP-4×90 P-4×60 RP-2.5D FS-2×30 FP-2×60 FP-2×90 P-3×60 RP-3 DFS. (4D refers to a transportelement having a length of 4 times the screw diameter of the feed screw type; 4×30 FP refers to 4 forward paddles positioned with mutual angle of 30 degrees, 4×60 RP refers to a working zone having reverse paddles positioned with a mutual angle of 60 degrees)

In this type of extruder the mixture is fed by a feeding screw turning a constant feeding speed (v1) (A feeding speed of 10 revolutions per minute amounts to a feeding speed of 1,5 kg per hour) onto the twin transporter screws having a diameter of 18 mm turning at a transporter speed (v2). These speeds are rotational speeds (revolutions per minute).

The mixture is then transported into a first heating zone (t1). Here the rate of transport diminished by a difference of the configuration of the twin transporter screws i.e. the rotational transporter speed v2 remains the same but the material does not progress as quickly.

Subsequently, the molten mass is transported by again normal configuration twin transporter screws to a second heating zone (t2) where the rate of transport is again diminished by a difference of configuration of the twin transporter screws.

After this second heating the thermomelting mixture is transported to the nozzle of the apparatus.

TABLE 1

| mixture | Batch. No | $t_1$ (° C.) | $t_2$ (° C.) | $t_p$ (° C.) | $v_1$ (rpm)* | $v_2$ (rpm)* |
|---|---|---|---|---|---|---|
| compound 1 : 1/3 HP-β-CD | 1 | 256 | 283 | 280 | 10 | 100 |
| itraconazole : 1/1 HP-β-CD | 2 | 263 | 265 | 279 | 10 | 20 |
| itraconazole : 1/3 HP-β-CD | 3 | 264 | 265 | 280 | 10 | 20 |
| loviride : 1/1 HP-β-CD | 4 | 274 | 285 | 292 | 10 | 80 |
| loviride : 1/3 HP-β-CD | 5 | 258 | 265 | 274 | 10 | 20 |

*rpm = revolutions per minute
$t_1$ : temperature of the first heating zone
$t_2$ : temperature of the second heating zone
$t_p$ : temperature inside the barrel
$v_1$ : rate of feeding screw
$v_2$ : twin transporter screws speed (rotational).

In every case the mixture of active ingredient and 2-hydroxypropyl-β-CD gave a solid solution.

EXAMPLE 2

Extruded samples of active ingredient with dimethyl-(β-cyclodextrin (DM-β-CD) were obtained using extruder type MP19-APV Baker with the process parameters as shown in the table 2.

TABLE 2

| mixture | Batch. No. | $t_1$ (° C.) | $t_2$ (° C.) | $t_p$ (° C.) | $v_1$ (1) (rpm) | $v_2$ (rpm)* |
|---|---|---|---|---|---|---|
| compound 1 : 1/1 DM-β-CD | 6 | 241 | 245 | 254 | 0 | 20 |
| itraconazole : 1/1 DM-β-CD | 7 | 239 | 240 | 253 | 0 | 20 |
| loviride : 1/1 DM-β-CD | 8 | 248 | 250 | 263 | 0 | 20 |

*rpm = revolutions per minute
(1) The apparatus was fed manually, without using the feeding screw. In every case the mixture of active ingredient and DM-β-CD.
$t_1$ : temperature of the first heating zone
$t_2$ : temperature of the second heating zone
$t_p$ : temperature inside the barrel
$v_1$ : feeding screw (rotational)
$v_2$ : twin transporter screws speed (rotational).

EXAMPLE 3

The dissolution of the melt extrudate of Batch No 1 was compared with the dissolution of the "physical mixture" (i.e. the mixture of the two component in the ratio as shown for Batch No. 1, but not melt extruded).

An amount of 100 mg of milled melt extrudate of Batch No 1 was added to a volume of 900 ml of artificial gastric juice at a temperature of 37 degrees Celsius. The stirring method used was the peddle method with a peddle moving at 100 rotations per minute. Using UV spectrometry the relative amount of dissolved extrudate was measured during 1 hour.

The same procedure for the "physical mixture" was followed.

The results of this dissolution process are shown in Table 3

TABLE 3

| time mixture (minutes) | milled extrudate Batch No 1 (% of total amount dissolved) | corresponding physical (% of total amount dissolved) |
|---|---|---|
| 0 | 0.00 | 0.00 |
| 5 | 62.10 | 1.71 |
| 15 | 70.20 | 14.67 |
| 30 | 72.63 | 21.06 |
| 45 | 74.07 | 26.10 |
| 60 | 74.25 | 28.35 |

EXAMPLE 4

The melting behavior was measured by using differential scanning calorimetry. The calorimeter used is the Perkin-Elmer 7 Series Thermal Analysis System. In all cases the rate of heating was set at 20 degrees Celsius per minute.

Figure 2:
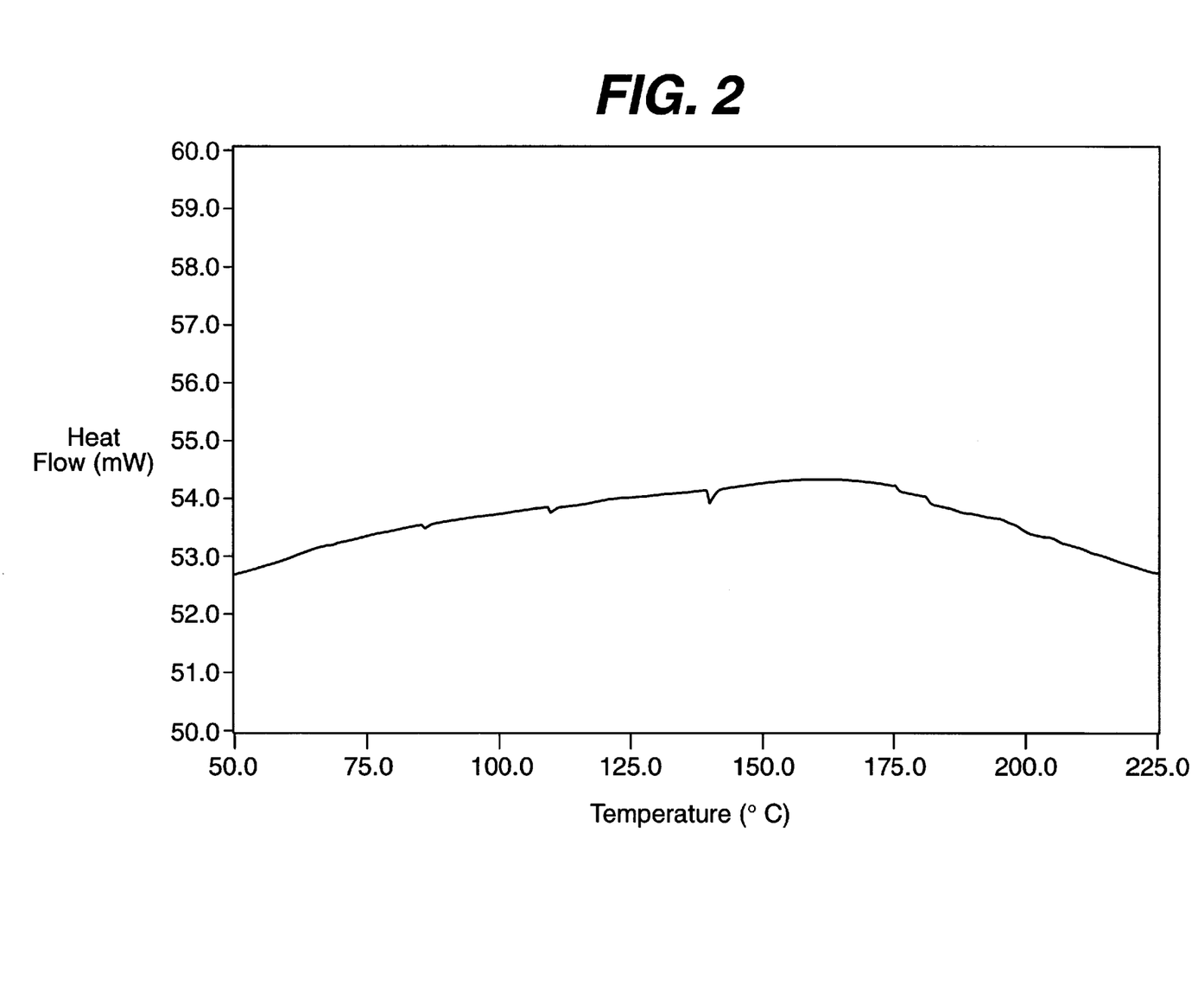
FIG. 2 is a differential scanning calorimetry curve (DSC curve) of non-milled Batch No 1 material. (see Example 1)

FIG. 2 shows the DSC curve of melt extrudate of Batch No 1 before milling. The curve shows no endothermic or exothermic peaks and it was established by visual inspection that the molten material was a clear solution, thus indicating that the non-milled melt extrudate of Batch No 1 is a solid solution.

Figure 3:
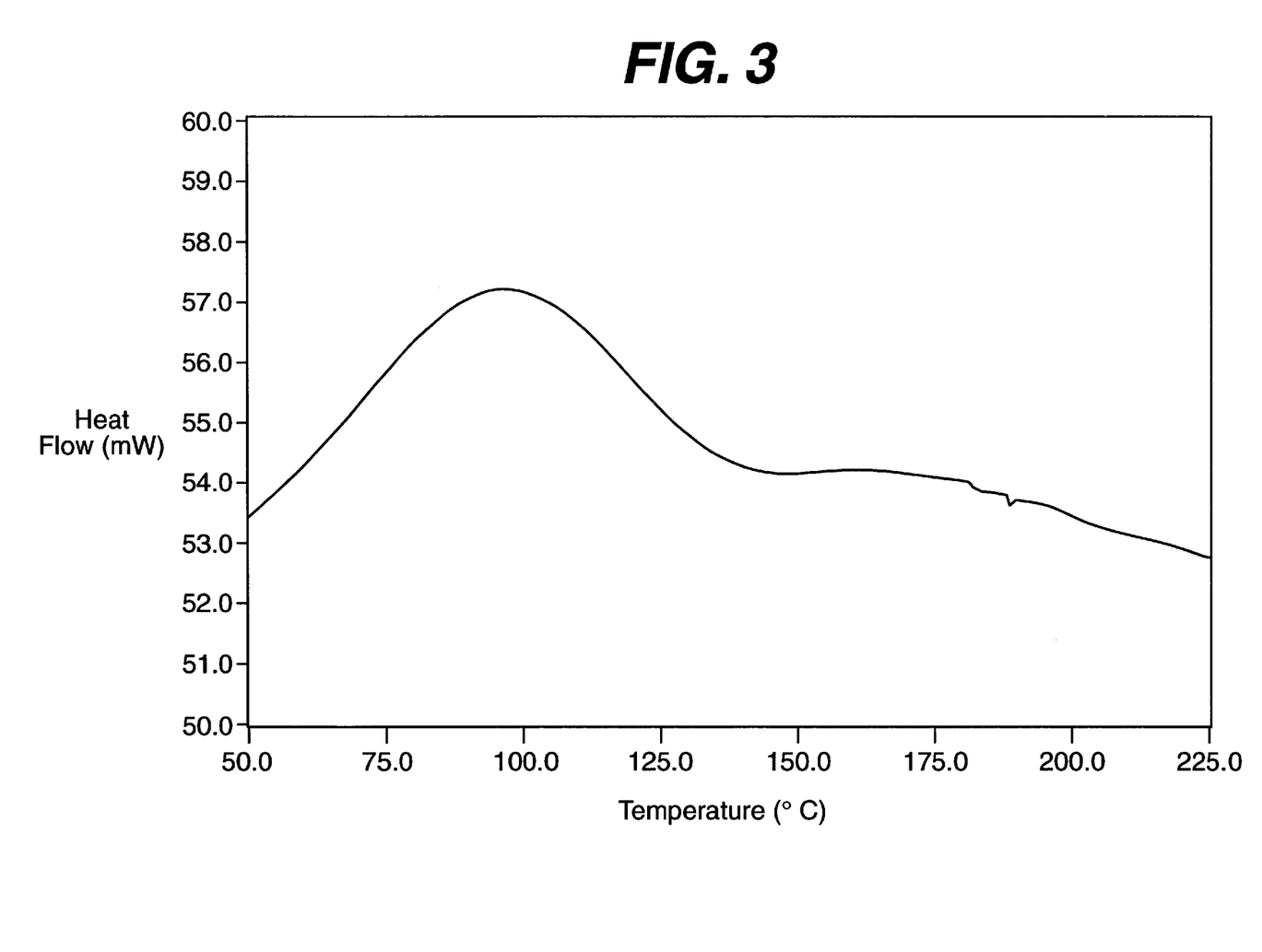
FIG. 3 is a differential scanning calorimetry curve of milled Batch No 1 material (see Example 1)

FIG. 3 shows the DSC curve of melt extrudate of Batch No 1 after milling. The curve shows no endothermic or exothermic peaks and it was established by visual inspection that the molten material was a clear solution, thus indicating that the milled melt extrudate of Batch No 1 is a solid solution.

Figure 4:
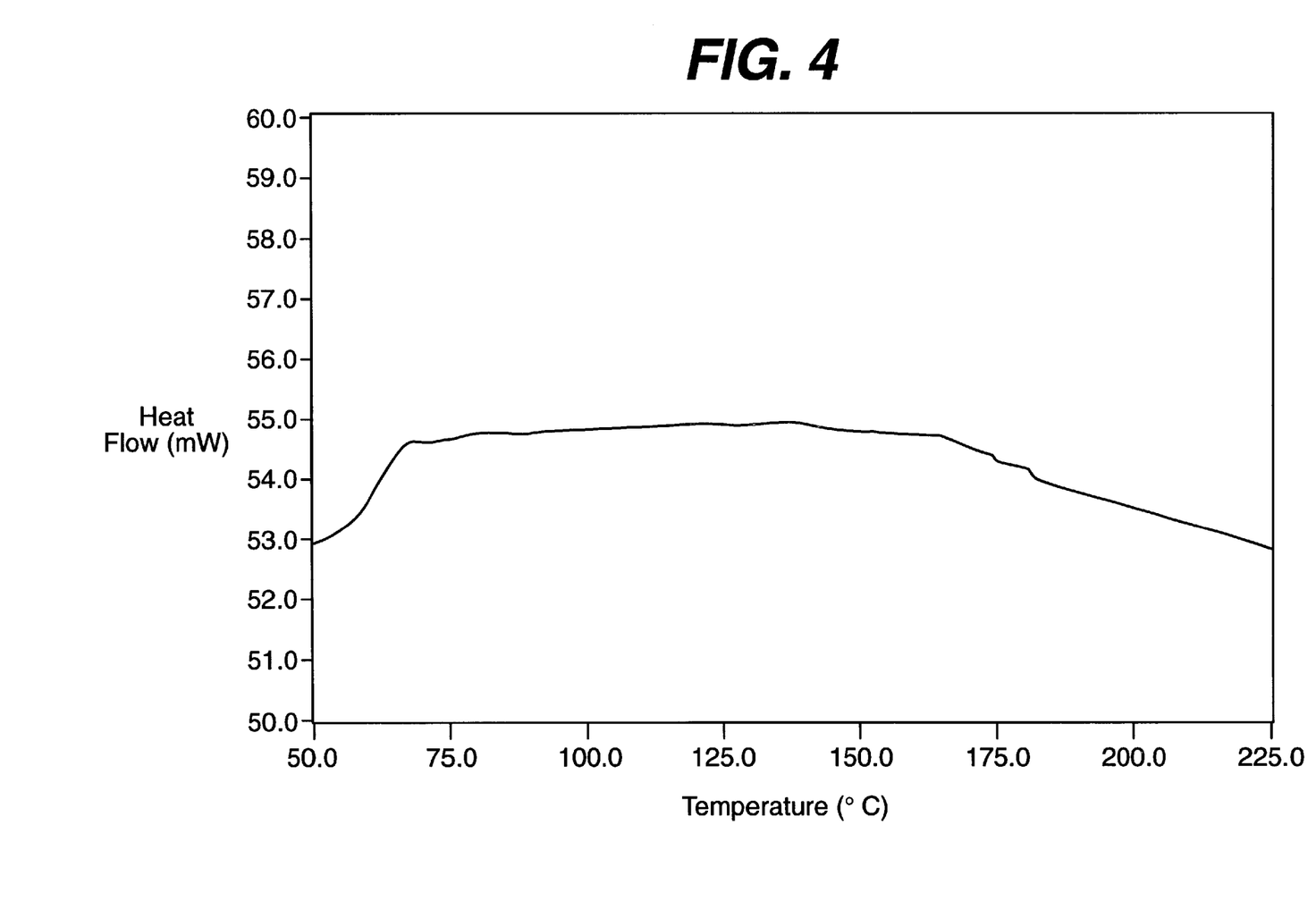
FIG. 4 is a differential scanning calorimetry curve of Batch No 2 material (see Example 1)

FIG. 4 shows the DSC curve of meltextrudate of Batch No 2 before milling. The curve shows no endothermic or exothermic peaks and it was established by visual inspection that the molten material was not a clear solution, thus indicating that the non-milled melt extrudate of Batch No 2 is a mixture of amorphous material.

Figure 5:
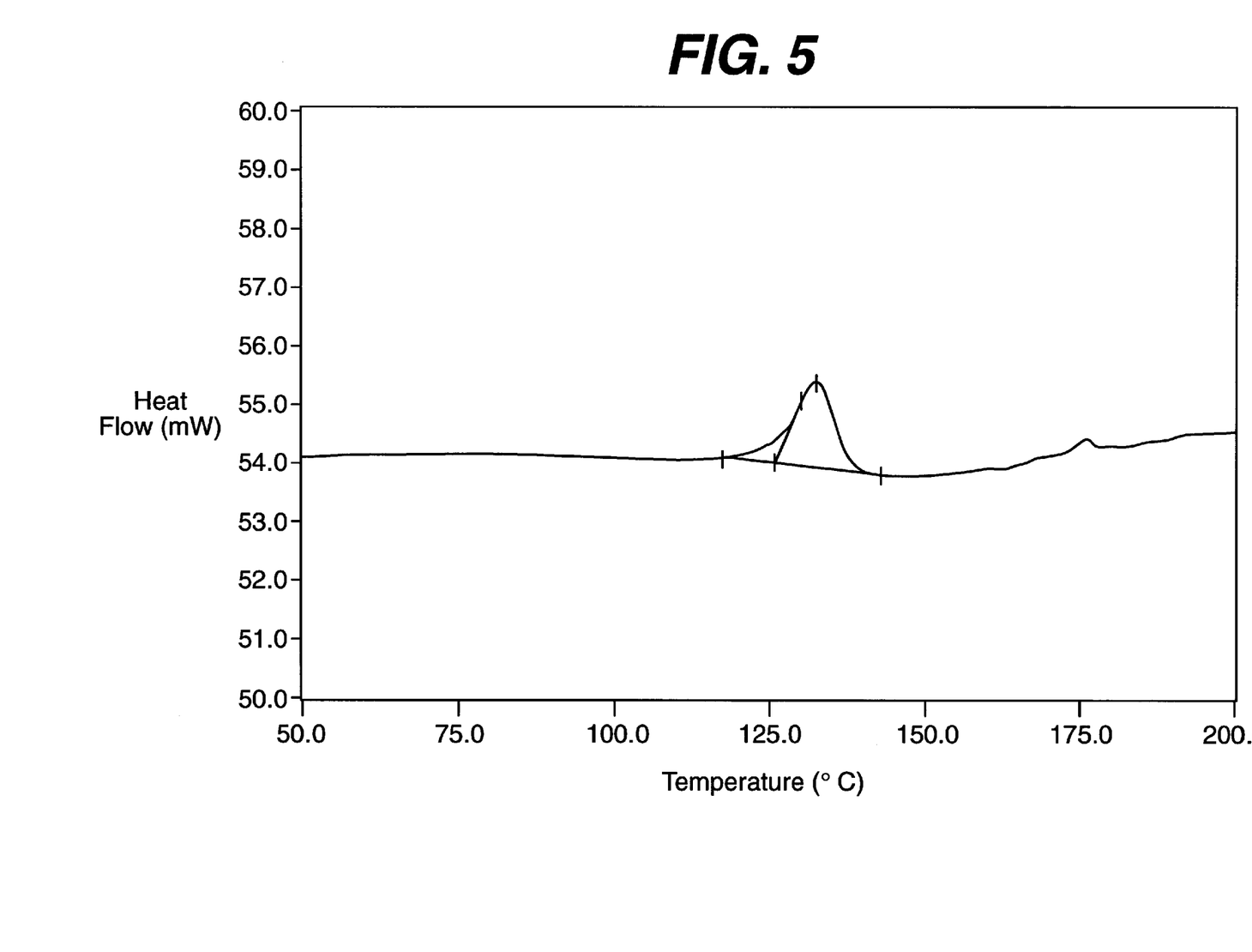
FIG. 5 is a differential scanning calorimetry curve of of Batch No 3 material (see Example 1)

FIG. 5 shows the DSC curve of meltextrudate of Batch No 3 before milling. The curve shows a small endothermic peak. The data on said small peak are as follows: X1=117.600 degrees Celsius, X2=143.200 degrees Celsius, Peak at 132.695 degrees Celsius, Area is 38.126 mJ, ΔH is 3.768 J/g, Height is 1.520 mW and the onset is at 125.816 degrees Celsius. Said small peak is very probably due to an impurity in the cyclodextrins. It was established that the non-milled melt extrudate of Batch No 3 is a mixture of amorphous material.

Figure 6:
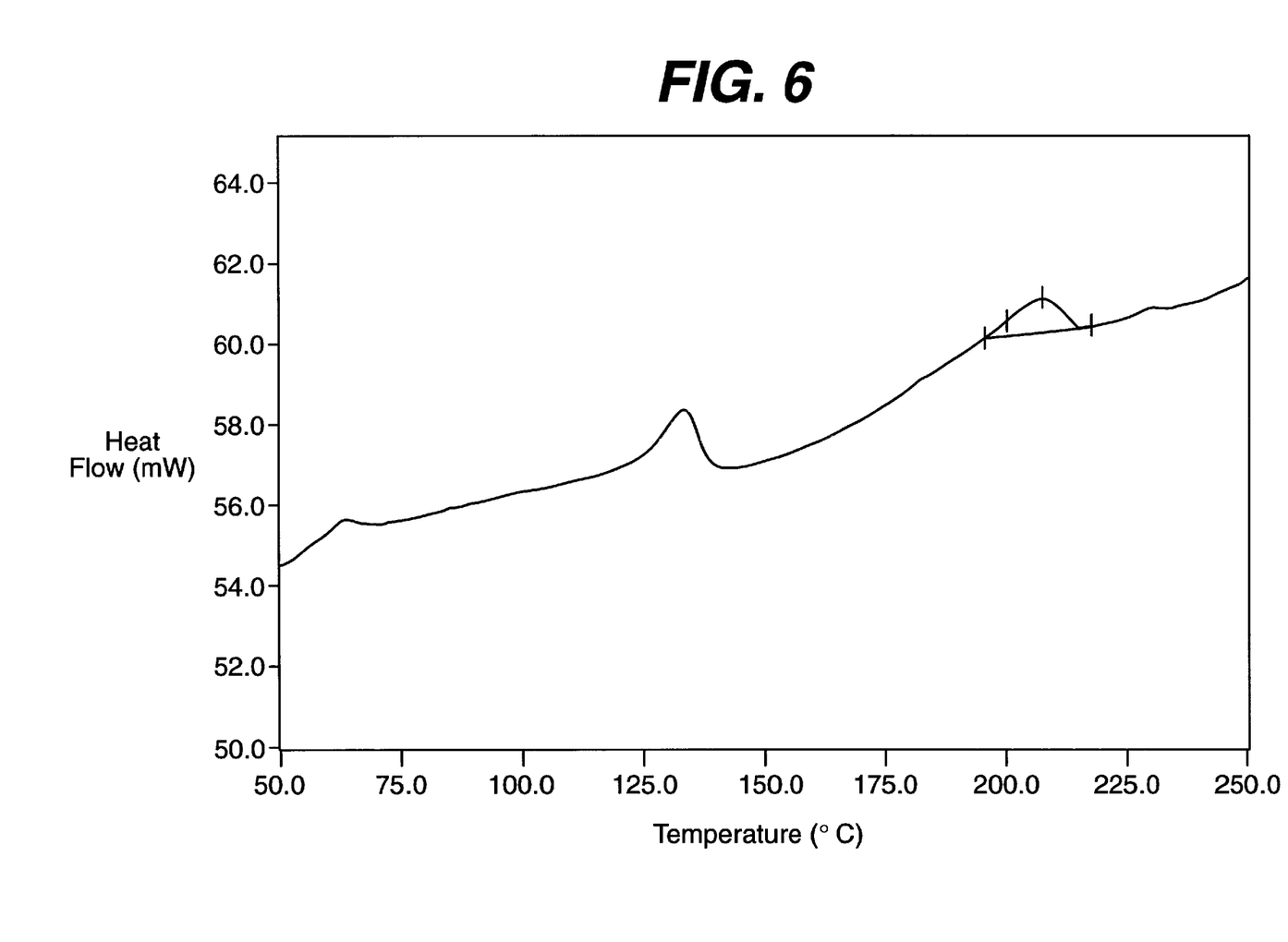
FIG. 6 is a differential scanning calorimetry curve of of Batch No 4 material (see Example 1)
Figure 7:
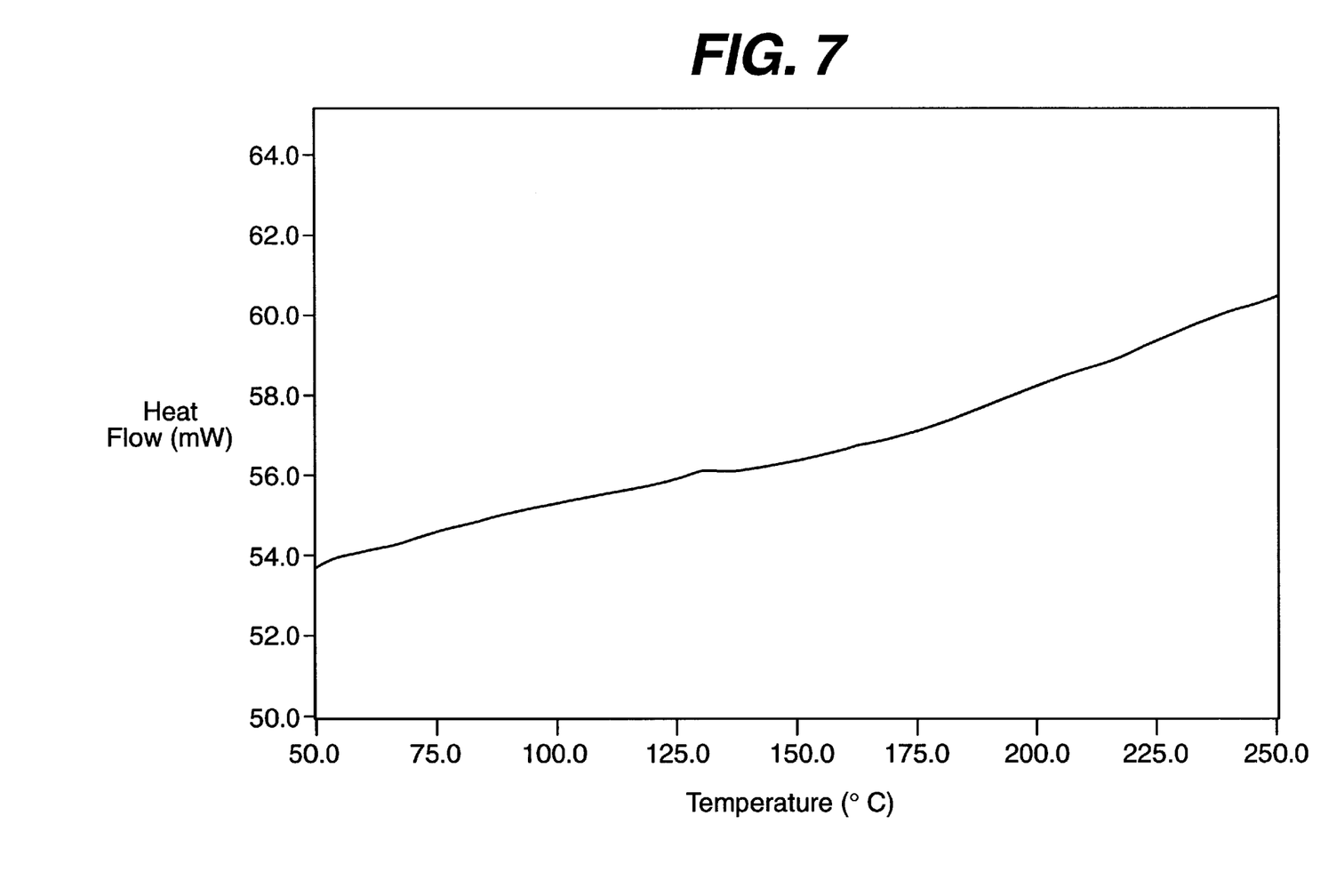
FIG. 7 is a differential scanning calorimetry curve of of Batch No 5 material (see Example 1)

FIG. 6 shows the DSC curve of meltextrudate of Batch No 4 before milling. The curve shows a few small endothermic peaks. Hence, it was established that the non-milled melt extrudate of Batch No 4 is a mixture of amorphous material containing small amounts of crystalline material FIG. 7 shows the DSC curve of meltextrudate of Batch No 5 before milling. The curve shows no endothermic or exothermic peaks and it was established by visual inspection that the molten material was not a clear solution, thus indicating that the non-milled melt extrudate of Batch No 5 is a mixture of amorphous material.

EXAMPLE 5

The melt extrudate of Batch No. 1 was milled and sieved. By mixing the appropriate amounts a tablet having the following composition was prepared in an art-known way:

| | |
|---|---|
| milled extrudate batch No 1 | 480 mg |
| microcrystalline cellulose | 218 mg |
| Aerosil | 3 mg |
| magnesium stearate | 5 mg |
| crospovidone | 144 mg |

What is claimed is:

1. Process for preparing a solid mixture for pharmaceutical, therapeutic or cosmetic forms such as tablets or capsules comprising one or more cyclodextrins and itraconazole characterized in that said process encompasses a melt-extrusion step, wherein the itraconazole is embedded into the cyclodextrin carrier.

2. A process as claimed in claim 1, wherein the melt-extrusion process comprises the following substeps:
   a) mixing one or more cyclodextrins with one or more active ingredients, and
   b) optionally mixing additives;
   c) heating the thus obtained mixture until melting of one of the components;
   d) forcing the thus obtained mixture through one or more nozzles;
   e) cooling the mixture till it solidifies.

3. A solid mixture made by the process of claim 1.

4. A solid mixture as claimed in claim 3 characterized in that the active ingredient or active ingredients are insoluble according to the definition of US Pharmacopeia.

5. A solid mixture as claimed in claim 3, wherein substantially only one type of cyclodextrin is present.

6. A solid mixture as claimed in claim 3 wherein a cyclodextrin is hydroxypropyl-β-cyclodextrin.

7. A solid mixture as claimed in claim 3 wherein a cyclodextrin is dimethyl-β-cyclodextrin.

8. A pharmaceutical composition comprising a powdered form of the solid mixture of claim 3 and other excipients.

9. A process for preparing a pharmaceutical composition comprising milled melt extrudate and other pharmaceutically acceptable excipients characterized by milling appropriately the solid mixture as claimed in claim 4, intimately mixing the thus obtained powdered material with the other pharmaceutically acceptable excipients and further processing into pharmaceutical dosage forms.

* * * * *